US009205276B2

(12) United States Patent
Romanczyk et al.

(10) Patent No.: US 9,205,276 B2
(45) Date of Patent: Dec. 8, 2015

(54) LIGHT AS A REPLACEMENT FOR MITOGENIC FACTORS ON PROGENITOR CELLS

(75) Inventors: Tara B. Romanczyk, San Diego, CA (US); Juanita J. Anders, Potomac, MD (US); Ronald R. Waynant, Clarksville, MD (US); Ilko K. Ilev, Rockville, MD (US); Leonardo Longo, Florence (IT)

(73) Assignees: THE HENRY M. JACKSON FOUNDATION FOR THE ADVANCEMENT OF MILITARY MEDICINE, INC., Bethesda, MD (US); THE UNITED STATES OF AMERICA, AS REPRESENTED BY THE SECRETARY OF THE DEPARTMENT OF HEALTH AND SERVICES, Washington, DC (US)

( * ) Notice: Subject to any disclaimer, the term of this patent is extended or adjusted under 35 U.S.C. 154(b) by 2010 days.

(21) Appl. No.: 11/909,145

(22) PCT Filed: Mar. 30, 2006

(86) PCT No.: PCT/US2006/011573
§ 371 (c)(1),
(2), (4) Date: Oct. 26, 2009

(87) PCT Pub. No.: WO2006/105254
PCT Pub. Date: Oct. 5, 2006

(65) Prior Publication Data
US 2010/0055074 A1    Mar. 4, 2010

Related U.S. Application Data

(60) Provisional application No. 60/666,582, filed on Mar. 31, 2005.

(51) Int. Cl.
| *A01N 63/00* | (2006.01) |
| *A61N 5/06* | (2006.01) |
| *A61K 41/00* | (2006.01) |
| *C12N 5/0797* | (2010.01) |
| *C12N 13/00* | (2006.01) |

(52) U.S. Cl.
CPC .............. *A61N 5/0601* (2013.01); *A61K 41/00* (2013.01); *C12N 5/0623* (2013.01); *C12N 13/00* (2013.01); *A61N 2005/0659* (2013.01); *C12N 2501/11* (2013.01); *C12N 2501/115* (2013.01)

(58) Field of Classification Search
None
See application file for complete search history.

(56) References Cited

U.S. PATENT DOCUMENTS

| 2,637,322 | A | * | 5/1953 | Clay ............................... 607/90 |
| 5,347,134 | A | * | 9/1994 | Hashimoto et al. ......... 250/492.1 |
| 5,626,861 | A | * | 5/1997 | Laurencin et al. ............ 424/426 |
| 5,639,402 | A | * | 6/1997 | Barlow et al. ..................... 264/6 |
| 5,989,245 | A | * | 11/1999 | Prescott .......................... 606/14 |
| 6,312,451 | B1 | * | 11/2001 | Streeter ........................... 607/89 |
| 6,471,961 | B1 | * | 10/2002 | Tobinick ..................... 424/134.1 |
| 2001/0038836 | A1 | * | 11/2001 | During et al. ................ 424/93.7 |
| 2004/0186087 | A1 | * | 9/2004 | Grafe et al. .................... 514/185 |
| 2004/0266748 | A1 | * | 12/2004 | Robinson et al. ............. 514/185 |
| 2005/0260710 | A1 | * | 11/2005 | Suzuki et al. ................. 435/69.1 |
| 2006/0057712 | A1 | * | 3/2006 | Yamashita et al. .......... 435/303.1 |

FOREIGN PATENT DOCUMENTS

| WO | WO 98/04321 A1 | 2/1998 |
| WO | WO 03/060082 A2 | 7/2003 |
| WO | WO 2004/090092 | * 10/2004 | .............. C12M 3/00 |
| WO | WO 2005/025672 A1 | 3/2005 |

OTHER PUBLICATIONS

Abramovitch-Gottlib et al. 2005. Low level laser irradiation stimulates osteogenic phenotype of mesenchymal stem cells seeded on a three-dimensional biomatrix. Laser Med Sci 20: 138-146.*
Kim HK et al. 2009. Red light of 647 nm enhances osteogenic differentiation in mesenchymal stem cells. Laser Med Sci 24; 214-222.*
Hui et al. 2005. Surgery versus steroid injection in carpal tunnel syndrome: comment on the article by Ly-Pen et al. Arth Rheum 52: 2578.*
Ozawa Y et al. 1998. Low-Energy Laser Irradiation Stimulates Bone Nodule Formation at Early Stages of Cell Culture in Rat Calvarial Cells. Bone 22: 347-354.*
Pittenger MF et al. 1999. Multilineage Potential of Adult Human Mesenchymal Stem Cells. Science 284: 143-147.*
Basford JR et al. 1986. Comparison of Cold-Quartz Ultraviolet, Low-Energy Laser, and Occlusion in Wound Healing in a Swine Model. Arch Phys Med Rehabil 67: 151-154.*
Shihabuddin, L.S., et al., "The search for neural progenitor cells: prospects for the therapy of neurodegenerative disease," Molecular Medicine Today, vol. 5, pp. 474-480, Nov. 1999.
Anders, J.J., et al., "Low Power Laser Irradiation Alters the Rate of Regeneration of the Rat Facial Nerve," Lasers in Surgery and Medicine, vol. 13, pp. 72-82, 1993.

(Continued)

Primary Examiner — Lora E Barnhart Driscoll
(74) Attorney, Agent, or Firm — Foley & Lardner LLP

(57) ABSTRACT

The present invention generally relates to a method of using light treatment supporting specific cell types in a subject. Specifically, the present invention relates to methods for stimulating the proliferation, migration, differentiation and survival of cell using specific parameter of lights. These methods are particularly useful in the cellular regeneration and replacement in a tissue injury, such as CNS or PNS injury, and in transplantation of organs, tissues and cells.

14 Claims, 15 Drawing Sheets

(56) References Cited

OTHER PUBLICATIONS

Snyder, S.K., et al., "Quantitation of Calcitonin Gene-Related Peptide mRNA and Neuronal Cell Death in Facial Motor Nuclei Following Axotomy and 633 nm Low Power Laser Treatment," Lasers in Surgery and Medicine, vol. 31, pp. 216-222, 2002.

Mochizuki-Oda, N., et al., "Effects of near-infra-red laser irradiatin on adenosine triphosphate and adenosine diphosphate contents of rat brain tissue," Neuroscience Letters, vol. 323, pp. 207-210, 2002.

Saperia, D., et al., "Demonstration of Elevated Type I and Type III Procollagen mRNA Levels in Cutaneous Wounds Treated with Helium-Neon Laser," Biochemical and Biophysical Research Communications, vol. 138, No. 3, pp. 1123-1128, 1986.

Greco, M., et al., "Increase in RNA and Protein Synthesis by Mitochondria Irradiated with Helium-Neon Laser," Biochemical and Biophysical Research Communications, vol. 163, No. 3, pp. 1428-1434, 1989.

Lam, T.S., et al., "Laser Stimulation of Collagen Synthesis in Human Skin Fibroblast Cultures," Lasers in the Life Sciences, vol. 1, No. 1, pp. 61-77, 1986.

Funk, J.O., et al., "Cytokine productin after helium-neon laser irradiation in cultures of human peripheral blood mononuclear cells," J. Photochem. Photobiol. B: Biol., vol. 16, pp. 347-355, 1992.

Gage, F.H., "Mammalian Neural Stem Cells," Science, vol. 287, No. 5457, p. 1433, Feb. 25, 2000, as printed on Jan. 25, 2008.

Lindvall, O. (1991). Prospects of transplantation in human neurodegenerative diseases. Trends Neurosci. 14:376-84.

Mester et al. (1991). Photochemical effects of laser irradiation on neuritic outgrowth of olfactory neuroepithelial explants. Otolaryngol Head Neck Surg. 105:449-56.

Setoguchi et al. (2004).Treatment of spinal cord injury by transplantation of fetal neural precursor cells engineered to express BMP inhibitor. Exp Neurol. 189:33-44.

Wollman et al. (1996). Low power laser irradiation enhances migration and neurite sprouting of cultured rat embryonal brain cells. Neurol Res. 18:467-70.

International Search Report, International Patent Application No. PCT/US06/11573, filed Mar. 30, 2006.

Kao, B., et al., "Novel Model for Evaluation of Epidermal Preservation and Dermal Collagen Remodeling Following Photorejuvenation of Human Skin," Lasers in Surgery and Medicine (2003), vol. 32, pp. 115-119.

Medrano, A.R.A.P., et al., "Influence of Low Level Laser Therapy on Wound Healing and Its Biological Action Upon Myofibroblasts," Lasers in Surgery and Medicine (2003), vol. 32, pp. 239-244.

De Souza, S.C., et al., "Low power laser radiation at 685 nm stimulates stem-cell proliferation rate in *Dugesia tigrina* during regeneration," Journal of Photochemistry and Photobiology B: Biology (2005), vol. 80, pp. 203-207.

Vinck, E.M., et al., "Increased fibroblast proliferation induced by light emitting diode and low power laser irradiation," Lasers Med. Sci. (2003), vol. 18, pp. 95-99.

Kreisler, M., et al., "Low Level 809-nm Diode Laser-Induced in Vitro Stimulation of the Proliferation of Human Gingival Fibroblasts," Lasers in Surgery and Medicine (2002), vol. 30, pp. 365-369.

Schindl, A., et al., "Direct stimulatory effect of low-intensity 670 nm laser irradiation on human endothelial cell proliferation," British Journal of Dermatology (2003), vol. 148, pp. 334-336.

Grossman, N., et al., "780 nm Low Power Diode Laser Irradiation Stimulates Proliferation of Keratinocyte Cultures: Involvement of Reactive Oxygen Species," Lasers in Surgery and Medicine (1998), vol. 22, pp. 212-218.

Van Breugel, H.H.F.I., et al., "He—Ne laser irradiation affects proliferation of cultured rat Schwann cells in a dose-dependent manner," Journal of Neurocytology (1993), vol. 22, pp. 185-190.

Moore, P., et al., "Effect of Wavelength on Low-Intensity Laser Irradiation-Stimulated Cell Proliferation In Vitro," Lasers in Surgery and Medicine (2005), vol. 36, pp. 8-12.

Pal, G., et al., "Effect of low intensity laser interaction with human skin fibroblast cells using fiber-optic nano-probes," Journal of Photochemistry and Photobiology B: Biology (2007), vol. 86, pp. 252-261.

Zhang, X., et al., "Low-dose photodynamic therapy increases endothelial cell proliferation and VEGF expression in nude mice brain," Lasers in Medical Science (2005), vol. 20, pp. 74-79.

Liu et al. "Laser Biomodulation on Stem Cells" Proceedings of SPIE vol. 4427, pp. 31-35 (2001).

Byrnes et al., "Photobiomodulaton Improves Cutaneous Wound Healing in an Animal Model of Type II Diabetes," Photomedicine and Laser Surgery, vol. 22, No. 4, pp. 281-290, 2004.

Gasparyan et al., "Influence of Low Level Laser Radiation on Migration of Stem Cells," Proc. Of SPIE, vol. 5968, pp. 596808-1-596808-6, Jan. 1, 2005.

Pittenger et al., "Mesenchymal Stem Cells and Their Potential as Cardiac Therapeutics," Circulation Research, pp. 9-20, Jul. 9, 2004.

Peterson, "Stem cell therapy for neurological disease and injury," Panminerva Med, vol. 46, No. 1, pp. 75-80, Mar. 2004.

Ostenfeld et al., "Regional specification of rodent and human neurospheres," Developmental Brain Research, vol. 134, pp. 43-55, 2002.

Higuchi et al., "Visible light is able to regulate neurite outgrowth," J. Biomater. Sci. Polymer Edn., vol. 14, No. 12, pp. 1377-1388, Sep. 2003.

Shefer et al., "Primary Myogenic Cells See the Light: Improved Survival of Transplanted Myogenic Cells Following Low Energy Irradiation," Lasers in Surgery and Medicine, vol. 40, pp. 38-45, 2008.

Tuby et al., "Low-Level Laser Irradiation (LLLI) Promotes Proliferation of Mesenchymal and Cardiac Stem Cells in Culture," Lasers in Surgery and Medicine, vol. 39, pp. 373-378, 2007.

Tuby et al., "Implantation of Low-Level Laser Irradiated Mesenchymal Stem Cells into the Infarcted Rat Heart is Associated with Reduction in Infarct Size and Enhanced Angiogenesis," Photomedicine and Laser Surgery, vol. 27, No. 2, pp. 227-234, 2008.

Heil et al., "A Different Outlook on the Role of Bone Marrow Stem Cells in Vascular Growth," Circulation Growth, vol. 94, pp. 573-574, 2004.

Kinnaird et al., "Local Delivery of Marrow-Derived Stromal Cells Augments Collateral Perfusion Through Paracrine Mechanisms," Circulation, vol. 109, pp. 1543-1549, 2004.

Drummond-Barbosa, "Stem Cells, Their Niches and the Systemic Environment: An Aging Network," Genetics, vol. 180, pp. 1787-1797, Dec. 2008.

Titushkin et al., "Physicochemical Control of Adult Stem Cell Differentiation: Shedding Light on Potential Molecular Mechanisms," Journal of Biomedicine and Biotechnology, vol. 2010, Article ID 743476, Jan. 2010.

European Search Report issued on Jun. 4, 2012 in application No. EP 12 15 9277.

\* cited by examiner

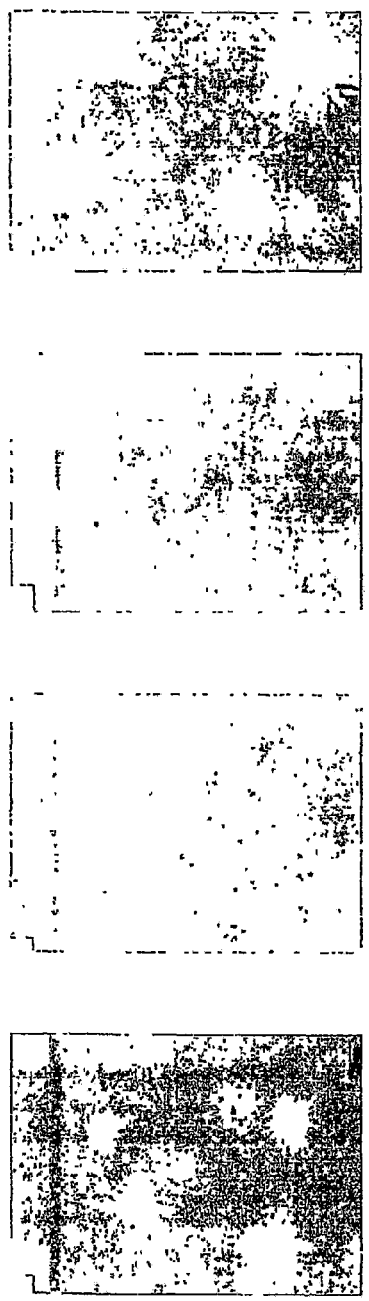
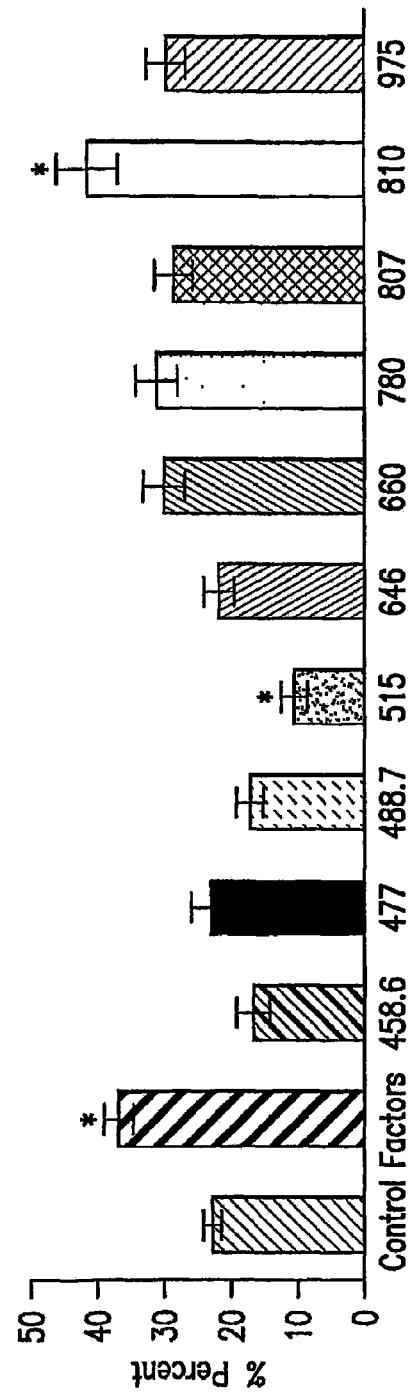

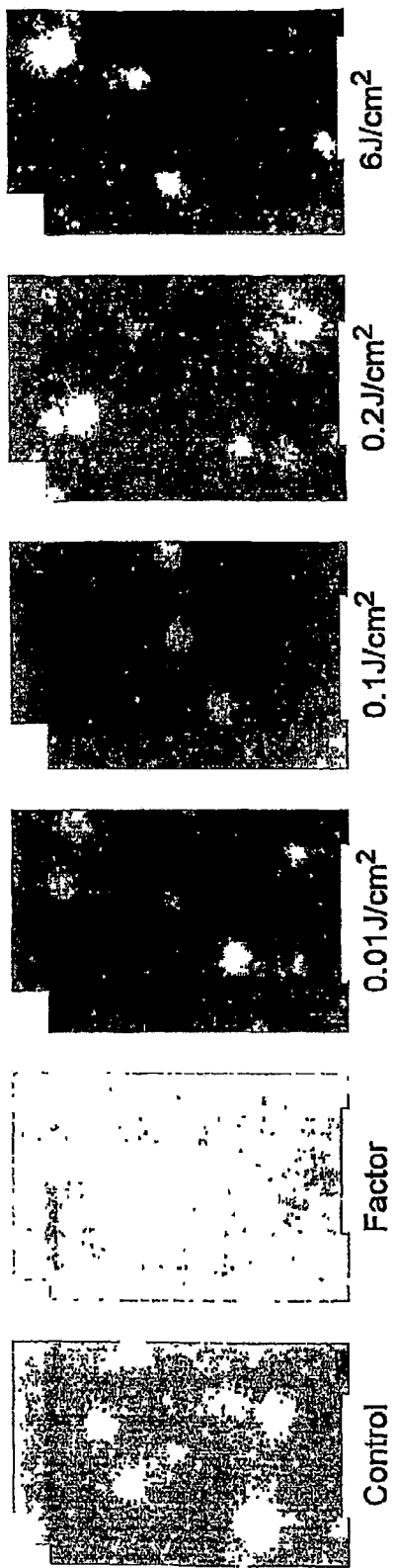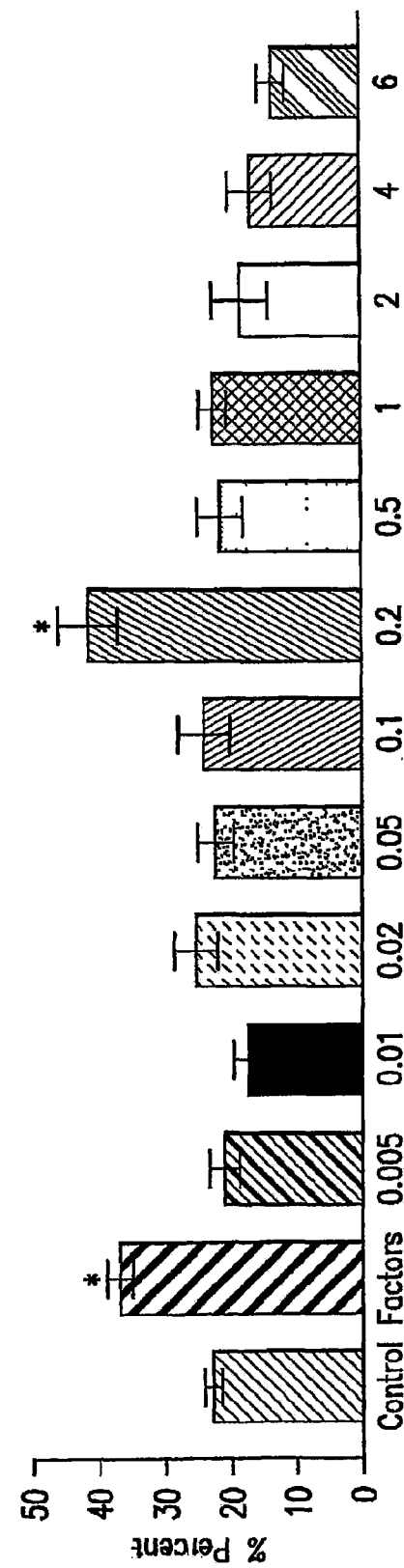

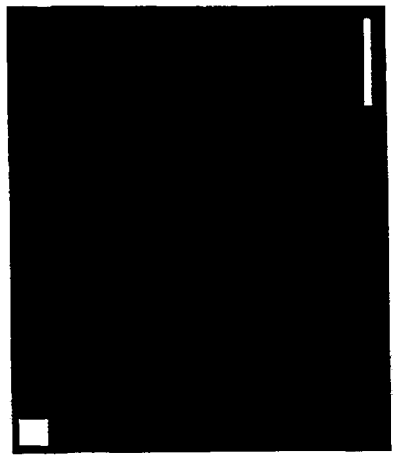
FIG.9A  FIG.9B  FIG.9C
FIG.9D  FIG.9E
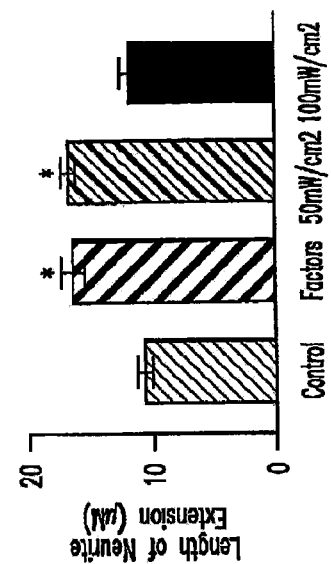
FIG.9F

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial
<220> FEATURE:
<223> OTHER INFORMATION: Synthetic primer

<400> SEQUENCE: 1
gccacatcta atctcatttc aca                                           23

<210> SEQ ID NO 2
<211> LENGTH: 20
<212> TYPE: DNA
<213> ORGANISM: Artificial
<220> FEATURE:
<223> OTHER INFORMATION: Synthetic primer

<400> SEQUENCE: 2
ctgggtaaca gcagatgcaa                                               20

<210> SEQ ID NO 3
<211> LENGTH: 23
<212> TYPE: DNA
<213> ORGANISM: Artificial
<220> FEATURE:
<223> OTHER INFORMATION: Synthetic primer

<400> SEQUENCE: 3
ctaatcacct actcaatgcc tgg                                           23

<210> SEQ ID NO 4
<211> LENGTH: 25
<212> TYPE: DNA
<213> ORGANISM: Artificial
<220> FEATURE:
<223> OTHER INFORMATION: Synthetic primer

<400> SEQUENCE: 4
tgattctccc agtactctta cttgg                                         25

<210> SEQ ID NO 5
<211> LENGTH: 25
<212> TYPE: DNA
<213> ORGANISM: Artificial
<220> FEATURE:
<223> OTHER INFORMATION: Synthetic primer

<400> SEQUENCE: 5
```

-continued

```
agcctcctct tctctttctg ctgga                                               25

<210> SEQ ID NO 6
<211> LENGTH: 25
<212> TYPE: DNA
<213> ORGANISM: Artificial
<220> FEATURE:
<223> OTHER INFORMATION: Synthetic primer

<400> SEQUENCE: 6
cttttgtcta tgcccctgca gcctt                                               25

<210> SEQ ID NO 7
<211> LENGTH: 25
<212> TYPE: DNA
<213> ORGANISM: Artificial
<220> FEATURE:
<223> OTHER INFORMATION: Synthetic primer

<400> SEQUENCE: 7
ccaagggagc agctttctat cctgg                                               25

<210> SEQ ID NO 8
<211> LENGTH: 25
<212> TYPE: DNA
<213> ORGANISM: Artificial
<220> FEATURE:
<223> OTHER INFORMATION: Synthetic primer

<400> SEQUENCE: 8
ggcagtgtca agggaatgct gaagt                                               25

<210> SEQ ID NO 9
<211> LENGTH: 22
<212> TYPE: DNA
<213> ORGANISM: Artificial
<220> FEATURE:
<223> OTHER INFORMATION: Synthetic primer

<400> SEQUENCE: 9
gtggcatcca cgaaactacc tt                                                  22

<210> SEQ ID NO 10
<211> LENGTH: 22
<212> TYPE: DNA
<213> ORGANISM: Artificial
<220> FEATURE:
<223> OTHER INFORMATION: Synthetic primer

<400> SEQUENCE: 10
ggactcgtca tactcctgct tg                                                  22
```

LIGHT AS A REPLACEMENT FOR MITOGENIC FACTORS ON PROGENITOR CELLS

This invention was made with United States Government support. The Government may have certain rights in the invention.

This application is a U.S. National Phase Application of International Application PCT/US2006/011573 (filed on Mach 30, 2006), which claims the benefit of U.S. Provisional Application 60/666,582 (filed on Mar. 31, 2005), the disclosures of which are herein incorporated by reference in their entirety.

A computer readable text file, entitled "044508-5031-US-SeqListing.txt," created on or about Sep. 22, 2009 with a file size of about 3 kb contains the sequence listing for this application and is hereby incorporated by reference in its entirety.

FIELD

The present invention generally relates to cell differentiation and medical treatment. Specifically, the present invention relates to methods for stimulating the proliferation, migration, differentiation and survival of cells using specific parameter of lights. These methods are particularly useful in the cellular regeneration and replacement in tissue injury and in transplantation of organs, tissues and cells.

BACKGROUND

Mitogenic factors are a requirement for the proliferation, migration, differentiation, maintenance and survival of multicellular organisms. The fate of many individual cells, e.g., proliferation, migration, differentiation, or interaction with other cells, is typically governed by information received from other cells and/or the immediate environment. This information is often transmitted by secreted polypeptides, such as mitogenic factors.

Stem cells are undifferentiated cells capable of (a) proliferation, (b) self maintenance, (c) the production of a large number of differentiated functional progeny, (d) regeneration of tissue after injury and/or (e) flexibility in the use of these options. Stem cells are important and ideal targets for gene therapy where the inserted genes promote the health of the individual into whom the stem cells are transplanted. Moreover, stem cells may play important roles in transplantation of organs or tissues, for example liver regeneration and skin grafting.

For example, neural stem cells (NSCs) are undifferentiated cells that have the ability to self renew and differentiate into neuronal and glial phenotypes. A primary concern in stem cell research is determining optimal conditions for the expansion of NSCs in clinically relevant numbers while maintaining normal karyotype and consistent differentiation capacities. The concept of a stem cell cellular differentiation is shown in FIG. 1 (Shihabuddin et al., *Mol Med Today Vol.* 5, (1999)). Presently, the only method to achieve expansion of NSCs is either by genetic modification to establish an immortalized cell line or by stimulating the cells with exogenous mitogenic factors such as fibroblast growth factor (FGF) and epidermal growth factor (EGF). Nonetheless, the cost of using a mitogenic factor as a therapeutical agent is expensive.

Light therapy (LT), also known as photo-biomodulation or low power laser irradiation (LPLI), is a non-invasive treatment which evokes biological effects via the absorption of light. LPLI has been shown to increase neuronal survival and regeneration in the peripheral nervous system (Anders, et al., *Surg. Med,* 13:72-82 (1993), Snyder, et al., *Surg. Med,* 31:216-222 (2002)). Investigation has shown that LT, through the absorption of light by a cellular photoreceptor, rather than heating of the cell (Anders, et al., *Surg Med.* 13:72-82, (1993), and Mochizuki-Oda, et al., *Neurosci. Lett.* 323:207-210 (2002)), can increase or decrease ATP, DNA, RNA and protein synthesis, depending on the treatment parameters applied (Saperia, et al., *Biochem. Biophys. Res. Commun.* 138:1123-1128 (1986); Greco, et al., *Biochem. Biophys. Res. Commun.* 163:1428-1434 (1989); Lam, et al., *Lasers Life Sci.* 1:61-77 (1986); Funk, et al., *J. Photochem. Photobiol. B:BBiol.* 16:347-355 (1992); Mochizuki-Oda, et al., Supra (2002)).

LT, however, has not been used as a replacement for mitogenic factors to support cellular survivability, proliferation, differentiation and migration.

SUMMARY

One aspect of the present invention is directed to methods for using light treatment as a replacement for mitogenic factors in stimulating cell differentiation, proliferation and migration. These methods are useful in a variety of clinical applications. In one embodiment, these methods are useful in the cellular regeneration and replacement in tissue injury, such as central nervous system (CNS) injury, peripheral nervous system (PNS) injury, neurodegenerative diseases and in transplantation of organs, tissues and cells.

In one embodiment, the methods for stimulating the proliferation, differentiation, and migration of cells and progenitors is achieved by using specific parameters of light which may include wavelength, power density and dosage.

In another embodiment, the method contains the step of exposing stem cells or progenitor cells to a light stimulation. The light stimulation is performed using a light source having a wavelength in the ultraviolet region, visible region, or infrared region, at a power density of 0.001-500 mW/cm$^2$, and a total light dosage of 0.001-100 J. The light stimulation may be performed in either an in vitro or in vivo setting.

In a preferred embodiment, the light stimulation is performed using a light source having a wavelength within the range of 200-1500 nm, a power density of either 0.5-150 mW/cm$^2$ and a total light dosage of 0.1-50 J.

In a more preferred embodiment, the light stimulation is performed using a light source having a wavelength of about 810 nm, a power density of either about 1 mW/cm$^2$, 50 mW/cm$^2$ or 100 mW/cm$^2$ and a total light dosage of about 0.2-10 J.

Another aspect of the present invention relates to a method for treating a disease in a mammal or a non-mammal using light stimulated cells, tissues or organs.

In one embodiment, the cells, tissues or organs are stimulated with light in vitro under conditions described above. The treated cells, tissues or organs are then transplanted into the diseased mammal or non-mammal.

In another embodiment, the cells, tissues or organs are stimulated with light in vivo in the diseased mammal or non-mammal.

Another aspect of the present invention relates to light treated cells, tissues and organs. The light treated cells, tissues and organs can be used for both research and clinical applications.

A better understanding of the present invention, its several aspects, and its advantages will become apparent to those skilled in the art from the following detailed description, taken in conjunction with the attached drawings, wherein there is shown and described the preferred embodiment of the invention, simply by way of illustration of the best mode contemplated for carrying out the invention.

BRIEF DESCRIPTION OF THE FIGURES

FIGS. 3A-3E illustrate the effect of light stimulation of different wavelengths on NHNPC surface area growth. FIGS. 3A-3D are images of NHNPCs under various treatment conditions shown in the figures. FIG. 3E is a graph summarizing the effect of various wavelengths NHNPCs. A surface area analysis was used to evaluate the growth of the NHNPCs. Twenty random regions were chosen per slide per group at a low optical power (10× objective) after fixation to quantify. Data are presented as mean±SEM.

FIG. 5A-5G shows the effect of light stimulation of different total light dosages on NHNPC surface area growth. The light treated slides were exposed to 810 nm light at dosages ranging from 0.005 $J/cm^2$ to 6 $J/cm^2$ once a day for three consecutive days. FIGS. 5A-5F are images of NHNPCs under various treatment conditions. FIG. 5G is a graph summarizing the effect of various dosages on NHNPCs growth.

FIG. 7A is the control group, grown in standard media (neural progenitor basal medium (NPBM) plus gentamycin sulfate). The Control group received no growth factors, serum or light treatment. NHNPCs in the Factor group (B) were grown in standard media plus human recombinant (hr) EGF (20 ng/ml), hrFGF-2 (20 ng/ml), and a proprietary serum provided by the company, Cambrex (Walkersville, Md.) called neural survival factor-1 (NSF-1). Cells in the Light groups, of 50 $mW/cm^2$ (C) and 100 $mW/cm^2$ (D) were grown in standard media and treated with 810 nm light at a dose of 0.2 $J/cm^2$ for three consecutive days.

FIG. 9 A-F shows the effect of growth factors and light treatment on NHNPC neurite extension. NHNPCs were placed into five groups: negative control (A), DCX Control (13), Factors (C), 50 $mw/cm^2$ (D) and 100 $mw/cm^2$ (E). The light treated slides were treated with 810 nm light for three consecutive days. All groups of cells were grown for a total of 7 days, fixed, processed for DCX (red) immunocytochemistry, and counterstained with DAPI (blue) to visualize nuclei. The negative control slide (A) did not contain any label for DCX. Bar=200 μm.

DETAILED DESCRIPTION

Figure 1:
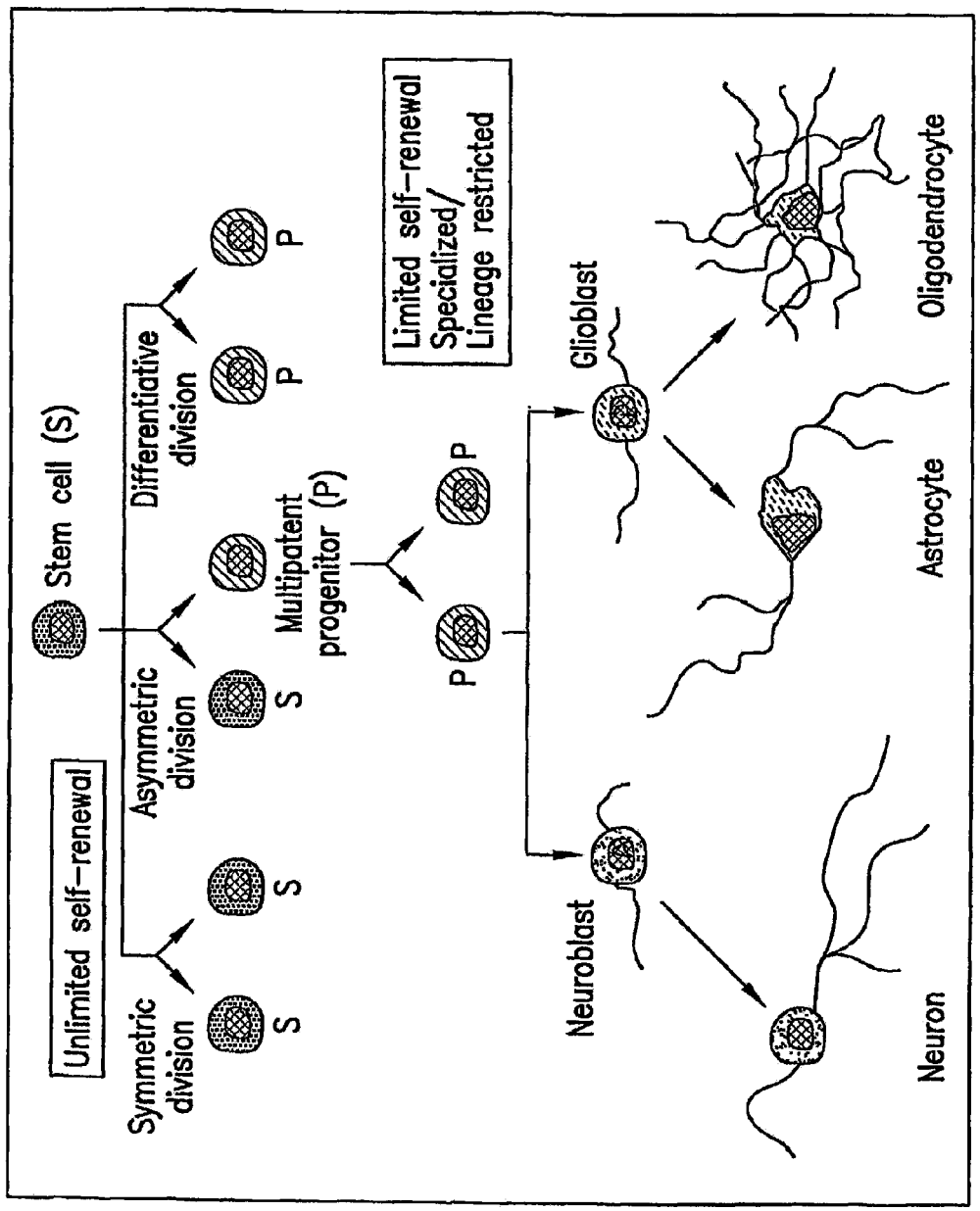
FIG. 1 is a schematic of the stem cell cellular differentiation.

The practice of the embodiments described in further detail below will employ, unless other wise indicated, conventional methods of microbiology, molecular biology, and immunology within the skill of the art. Such techniques are explained fully in the literature. All publications, patents and patent applications cited herein, whether supra or infra, are hereby incorporated by reference in their entirety.

One aspect of the present invention relates to methods for using light treatment as a replacement for mitogenic factors in stimulating cell differentiation, proliferation and migration.

The light treatment supports the survival, neurite outgrowth and migration of non-mammalian and mammalian cells, such as stem/progenitor cells. The light stimulation at specific wavelengths also causes neuronal stem/progenitor cells to differentiate into different neuronal phenotypes. The light treatment, therefore, can be used as a replacement for growth factors to 1) support cellular proliferation and survivability in tissue culture; 2) cause differentiation of stem/progenitor cells into different cell types (e.g., bone marrow stromal cells (BMSCs) can generate bone, cartilage, fat, tendon, muscle, and neural cells.); and 3) cause differentiation of stem/progenitor cells into specific cellular phenotypes (e.g., neuronal progenitors that generate specific neuronal phenotypes such as glutamatergic neurons, dopaminergic neurons, etc). The present invention can also be used for in vitro and in vivo for a variety of the medical applications. For instance, treating tissue injuries. It can be employed in the clinical setting in combination with transplantation techniques to support the replacement of specific cell types in the human body.

Accordingly, one aspect of the present invention relates to a method to stimulate the proliferation, differentiation, and migration of cells and progenitors using specific parameter of light which may include wavelength, power density and dosage. The light treated cells can be used in a variety of clinical and research applications.

In one embodiment, the method comprises the step of exposing stem cells or progenitor cells to a light stimulation. The stem cells or progenitor cells can be isolated stem or progenitor cells, such as neural progenitor cells, bone marrow stromal cells, mesenchymal stem cells, bone marrow mesenchymal stem cells, placental mesenchymal stem cells, peripheral blood derived mesenchymal stem cells, olfactory-derived stem cells, fat-derived stem cells, endothelial precursor and stem cells, hair follicle dermal stem cells, resident cardiac stem and progenitor cells, fetal liver stem/progenitor cells, and embryonic stem cells. The light stimulation may be performed in either an in vitro or in vivo setting.

In the in vitro setting, the cells are grown under proper tissue culture conditions, which typically require a specially designed culturing medium, a $CO_2$ rich, humidified environment, and an incubation temperature of about 37° C. Different progenitor/stem cells all require mitogens or growth factors although culturing conditions may vary. Specific culture conditions for various stem/progenitor cells may be found in Fred Gage et al., *Science* 287:1433-1438 (2000) and www.Worldhealth.net/p/1053,2161, which is hereby incorporated by reference in its entirety. The cultured cells are then plated or suspended at the proper density, and are subjected to the light stimulation.

The light stimulation is performed using a light source having a wavelength in the ultraviolet region, visible region, or infrared region, at a power density of 0.001-500 mW/cm$^2$, and a total light dosage of 0.001-100 J.

In a preferred embodiment, the light stimulation is performed using a light source having a wavelength within the range of 200-1500 nm, a power density of either 0.5-150 mW/cm$^2$ and a total light dosage of 0.1-50 J.

In a more preferred embodiment, the light stimulation is performed using a light source having a wavelength of about 810 nm, a power density of either about 1 mW/cm$^2$, 50 mW/cm$^2$ or 100 mW/cm$^2$ and a total light dosage of about 0.2-10 J.

The light stimulated cells are incubated under conditions that allow cell differentiation and proliferation. The differentiated cells can then be harvested, suspended at a proper concentration, and transplanted into a subject that will be benefited from such as cell transplantation. Methods and conditions of cell transplantation have been well established in the literature. In one embodiment, the light treated cells are human neural progenitor cells, and the subject is a subject having central nervous system (CNS) injury or peripheral nervous system (PNS) injury, such as spinal cord injury, stroke and traumatic brain injury. In another embodiment, the subject is a subject having a neurodegenerative disease and other diseases or conditions. The neurodegenerative disease includes but not limited to Parkinson's disease, Alzheimer's disease, Huntington's disease, Multiple Sclerosis, and ALS. Other diseases or conditions that may benefit from light-stimulated cell transplantation include, but are not limited to liver transplant, diabetes, and heart diseases, such as acute myocardial infarction.

In another embodiment, the stem and/or progenitor cells may also be exposed to light stimulation in an in vivo setting. A light source may be introduced to the treatment site through a catheter or a surgical procedure. The wavelength, power density and total light dosage may be optimized according to the location and the type of cells in need of stimulation.

Another aspect of the present invention relates to a method for treating a disease or condition in a mammal or non-mammal using light stimulated tissues or organs. In one embodiment, diseases and conditions treatable with the present invention include, but not limited to, CNS injury and PNS system injury, such as such as spinal cord injury, stroke and traumatic brain injury; neurodegenerative diseases, such as Parkinson's disease, Alzheimer's disease, Huntington's disease, Multiple Sclerosis, or ALS; diabetes and heart diseases, such as acute myocardial infarction.

In one embodiment, tissues or organs are stimulated with light in vitro under conditions described above. The light-treated tissues or organs are then transplanted into the diseased mammal or non-mammal.

In another embodiment, the tissues or organs are stimulated with light in vivo in the diseased mammal or non-mammal.

Another aspect of the present invention relates to light treated cells, tissues and organs. The light treated cells, tissues and organs can be used for clinical applications.

Advantage of the present invention includes, but are not limited to:

Cell preparation: Light will eliminate/replace the need for expensive growth factors.

Light at specific wavelengths may turn on the endogenous production of growth factors. This is important to the fields of regeneration and cellular replacement in a tissue injury, such as CNS or PNS injuries and other diseases that relates to the tissue injuries. It is also important to the fields of transplantation of organs, tissues and cells.

Specific wavelengths of light may cause pluripotent cells to be "forced" into specific types of cells, which again would be important to the fields of regeneration and cellular replacement in a tissue injury, such as CNS or PNS injuries and diseases and to the fields of transplantation of organs, tissues and cells.

The present invention is further illustrated by the following examples which should not be construed as limiting. The contents of all references, patents and published patent applications cited throughout this application, as well as the Figures and Tables are incorporated herein by reference.

Example 1

Material and Methods (a) NHNP Cell Culture Preparation

Figure 2:
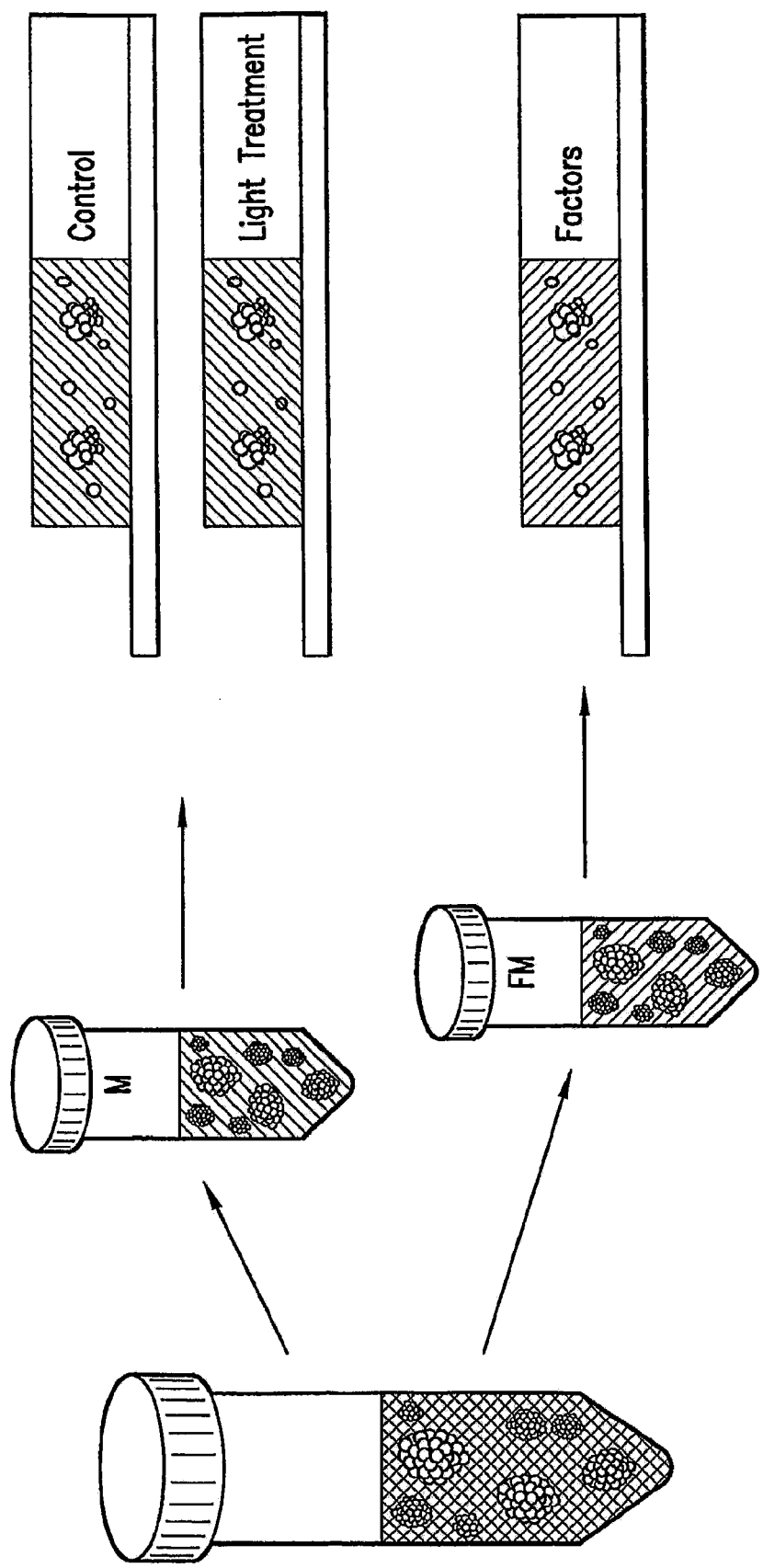
FIG. 2 illustrates the general experimental design for optimization of parameters of light treatment.

The NHNP culture process is shown in FIG. 2. Generally, normal human neural progenitor cells (NHNPCs) were given media with factors (FM) containing human recombinant (hr)

EGF, hrFGF-2, and neural survival factor-1, or media without factors (M). Both types of media contained antibiotics. Cells were plated at a seeding density of ~25,000 cells/cm$^2$ on 2-chamber slides coated with either polyethleneimine (PEI) or laminin.

Briefly, the NHNP cells were thawed in a 37° C. water bath for 1-2 minutes, resuspended in warn (37° C.) neural progenitor maintenance media (NPMM), and incubated (24 hours, 37° C., 5% $CO_2$). The NPMM contained gentamycin sulfate, human recombinant (hr) EGF, hrFGF-2, and neural survival factor-1 (NSF-1). The cells were transferred into 50 ml plastic tubes and centrifuged (1000 rpm, 5 min). The supernatant was removed and the pellet was resuspended in either neural progenitor basal medium (NPBM) (for control and light-treated slides) or NPMM (for factor slides). NPBM contained all the same ingredients as NPMM except the growth factors and NSF-1. The cells were plated on either polyethyleneimine (PEI) or laminin coated-chamber slides at a seeding density of ~25,000 cells/cm$^2$. All products were purchased from Cambrex (Walkersville, Md.).

b) Optimal Parameter Assessment: Wavelength, Power Density, and Dosage

NHNPCs were plated on slides and treated with light once a day for three days and grown for a total of seven days in three separate experiments using the following conditions: 1) Wavelengths: 458.6, 477, 488.7, 515, 646, 660, 780, 807, 810, and 975 nm; 2) Dosage (810 nm light): 0.005, 0.01, 0.02, 0.05, 0.1, 0.2, 0.5, 1, 2, 4, and 6 J/cm$^2$; and 3) Power density (810 nm light, 0.2 J/cm$^2$): 1, 3, 10, 30, 50, and 100 mW/cm$^2$. For each of the three experiments, the spot size diameter of the laser(s) was 10 mm, the area was 0.785398 cm$^2$, and a minimum of two slides containing NHNPCs per experimental group was used. Additionally, each experiment had two Control (no light, no growth factors) and Factors (growth factors only, no light), slides. A surface area analysis was used to evaluate the growth of the NHNPCs after the conclusion of each experiment. Twenty random regions were chosen per slide per group at a low optical power (10× objective) using a Nikon (Tokyo, Japan) microscope, after fixation to quantify. Data are presented as mean±SEM.

c) Light Treatment

NHNPCs were separated into four groups: Control (no light, no growth factors), Factors (growth factors only, no light), 50 mW/cm$^2$ (light only, no growth factors), and 100 mW/cm$^2$ (light only no growth factors). All light-treated NHNPCs were exposed to an 810 nm 150 mW diode laser at a dose of 0.2 J/cm$^2$ each day for 3 days at a power density of either 50 mW/cm$^2$ for 4 seconds or 100 mW/cm$^2$ for 2 seconds.

d) Cell Proliferation Activity Assay

Cell proliferation of NHNPCs was determined using the CellTiter 96® AQ$_{ueous}$ One Solution Cell Proliferation Assay (MTS) (Promega, Madison, Wis.) and the Cyquant Cell Proliferation Assay Kit (Molecular Probes, Inc., Eugene, Oreg.) according to the manufacturers. Cells used in the Promega and Cyquant proliferation assays were grown accordingly: Cells in the Standard media group were grown in standard media (NPBM plus gentamycin sulfate). Cells in the Standard media+serum group were grown in standard media plus NSF-1 (serum). Cells in the Standard media+factors+serum group were grown in standard media plus hrEGF (20 ng/ml), hrFGF-2 (20 ng/ml), and neural survival factor-1. Cells in the Standard media+Light group were grown in standard media and treated with light (810 nm, 0.2 J/cm$^2$, 50 mW/cm$^2$) for three consecutive days. Cells for both the Promega and Cyquant assays were plated on uncoated-24-well plates at a seeding density of ~25,000 cells/cm$^2$.

e) Migration Assay

The QCM 24-Well Colorimetric Cell Migration Assay (Chemicon, Temecula, Calif.) was used according to the manufacturer. Naïve NHNPCs, defined as NHNP cells that were not exposed to growth factors, serum or light treatment. These cells were starved in serum and factor free media for 18-24 hrs prior to the assay. The cell suspension was removed and placed inside an insert which was then placed into a 24-well plate well containing one of four types of attractant medium: 1) Starvation media: contains no growth factors or serum; 2) Growth Factor media: contains EGF and FGF-2; 3) Light Conditioned Cell Media: media taken from cells exposed to 810 nm, 50 mW/cm$^2$ light, 0.2 J/cm$^2$ for three consecutive days; or 4) Light Treated Starvation Media: starvation media treated with 810 nm, 50 mW/cm$^2$ light, 0.2 J/cm$^2$ for three consecutive days. The plates were then incubated for 24 hours at 37° C. in a $CO_2$ incubator (4-6% $CO_2$). The cells/media from the top side of the insert were removed by pipetting out the remaining cell suspension. The migration insert was then placed into a clean well containing Cell Stain and incubated for 20 minutes at room temperature. The insert was removed from the cell stain and dipped into sterile water several times to rinse and a cotton-tipped swab was used to gently remove non-migratory cells from the interior of the insert and allowed to dry. The stained insert was transferred to a well containing extraction buffer and incubated at room temperature for 15 minutes and then removed. The dye mixture was transferred to a 96-microtiter plate and the optical density was measured at 560 nm.

f) Statistics

The statistical software program GraphPad Prism version 3.02 for Windows (GraphPad Software, San Diego, Calif., www.graphpad.com) was used for data analysis. Statistical comparisons were performed using one-way analysis of variance (ANOVA) followed by Tukey's post-test for comparison of individual groups. Data are presented as mean±SEM.

g) Immunostaining

Cultured NHNPCs were fixed in 4% paraformaldehyde (Sigma) in phosphate buffered saline (PBS) for 10 minutes at room temperature four days after the last day of light treatment. The cells were rinsed and stored in PBS. For immunostaining, the cells were treated with primary antibody for 1 hr at 4° C. for the doublecortin, or overnight at 4° C. for all other antibodies. The primary antibodies employed and their dilutions were as follows: nestin monoclonal (1:100, Chemicon, Temecula, Calif.); musashi polyclonal (1:200, Chemicon, Temecula, Calif.); glial fibrillary acidic protein (GFAP) polyclonal (1:300, DAKO, Carpinteria, Calif.), anti-β-tubulin isotype III (TUJ1) monoclonal (1:75, Sigma, St. Louis, Mo.); FGF-2 polyclonal (1:100, Santa Cruz Biotechnology Inc., Santa Cruz, Calif.) and Doublecortin (DCX) polyclonal (1:3000, Chemicon, Temecula, Calif.). For the detection of primary antibodies, fluorescein (FITC)-, or CY3-labeled secondary antibodies (Jackson Immunoresearch Laboratories, West Grove, Pa.) were used according to the manufacturer's specifications. Slides were mounted in vectashield with a DAPI mounting medium (Vector Laboratories, Burlingame, Calif.) for fluorescence and coverslipped. No primary antibody was added for negative control slides. Slides were photographed using a Nikon (Tokyo, Japan) Labophot fluorescent microscope, and images were captured using a Sony (Tokyo, Japan) DKC 5000 Catseye digital still camera.

h) RT-PCR

NHNPCs were placed into four groups: Control, Factors, Light (3 days), and Light (7 days). The Light Treated slides were treated (810 nm light, 50 mw/cm$^2$, 0.2 J/cm$^2$) for three consecutive days. All groups, with the exception of the Light (3 days) were grown for a total of 7 days. Total cellular RNA was extracted and reverse transcribed using First-Strand Synthesis beads Marsha Pharmacia, Piscataway, N.J.) as per the protocol of the manufacturers (Nitrogen, Carlsbad, Calif. and Amersham Pharmacia). Briefly, cells were lysed by the addition of TRIzol. RNA was extracted using the chloroform/isopropanol method and purified with 75% ethanol prior to being resuspended. RNA was transferred to tubes containing First-Strand Synthesis beads (Amersham Pharmacia) and Random Hexamers (Invitrogen) and incubated at 1 hour at 37° C. Resultant cDNA was amplified using the following primers: FGF-2 (5'-GCC ACA TCT AAT CTC ATT TCA CA-3' (SEQ ID NO:1); 5'-CTG GGT AAC AGC AGA TGC AA-3'(SEQ ID NO:2)), EGF (5'-CTA ATC ACC TAC TCA ATO CCT GG-3'(SEQ ID NO:3); 5'-TGA TTC TCC CAG TAC TCT TAC TTG G-3' (SEQ ID NO:4)), BDNF (5'-AGC CTC CTC TTC TCT TTC TGC TGG A-3' (SEQ ID NO:5); 5'-CTT TTG TCT ATG CCC CTG CAG CCT T-3'(SEQ ID NO:6)), NGF (5' CCA AGG GAG CAG CTT TCT ATC CTG G 3' (SEQ ID NO:7), 5' GGC AGT GTC AAG GGA ATG CTG AAG T 3' (SEQ ID NO:8)) and β-actin (5'-GTG GCA TCC ACG AAA CTA CCT T-3' (SEQ ID NO:9), 5'-GGA CTC GTC ATA CTC CTG CTT G-3' (SEQ ID NO:10)).

(i) Quantification of Neurite Outgrowth

The effects of different treatment applications on neurite outgrowth in the four groups were analyzed following doublecortin (DCX) immunocytochemistry. DCX is a phosphoprotein that is widely expressed in the CNS and is present in young migrating and differentiating neurons. Slides were analyzed using Neuron J in Image J (http://rsb.info.nih.gov/ij/). For each slide, a minimum of five random neurospheres were selected and imaged using a Nikon Labophot fluorescent microscope, and images were captured using a Sony DKC 5000 Catseye digital still camera. All processes were measured. Data are presented as mean±SEM.

Example 2

Optimization of Light Treatment Parameters in NHNP Cells

Normal human neural progenitor (NHNP) cells are obtained cryopreserved from Cambrex (Walkersville, Md.). Optimal light treatment parameters were identified through a series of experiments using the NHNP cells. These parameters included determining the optimal 1) wavelength, 2) power density, and 3) dosage. All slides in all experiments contained the NHNP cells and were treated with specific light parameters once a day for three consecutive days. At the completion of the treatment regiment, cells were fixed in 4% paraformaldehyde for 10 minutes and maintained in PBS for further processing and analysis. Control slides received no light treatment and did not contain any growth factors or serum. The Factor slides were not exposed to light treatment, but they did contain growth factors (fibroblast growth factor-2 (FGF-2) and epidermal growth factor (EGF)) and serum. FGF-2 and EGF both stimulate cells and cause cellular proliferation, but neither is required for differentiation. All other slides were light treated slides and did not contain growth factors.

The assay used to evaluate the NHNP cells under each treatment condition was a surface area count. Using a reticule, slides were assessed at the completion of the treatment regiment, at 10× magnification on our Nikon microscope. The size of the reticule box at a magnification of 10× is 1 mm2. Twenty measurements were obtained from each slide. The surface area (mm2) covered by the NHNP cells in the reticule box was measured and statistical analysis was performed using a one-way ANOVA and Tukey Post hoc test.

Optimal Parameters

Figure 4:
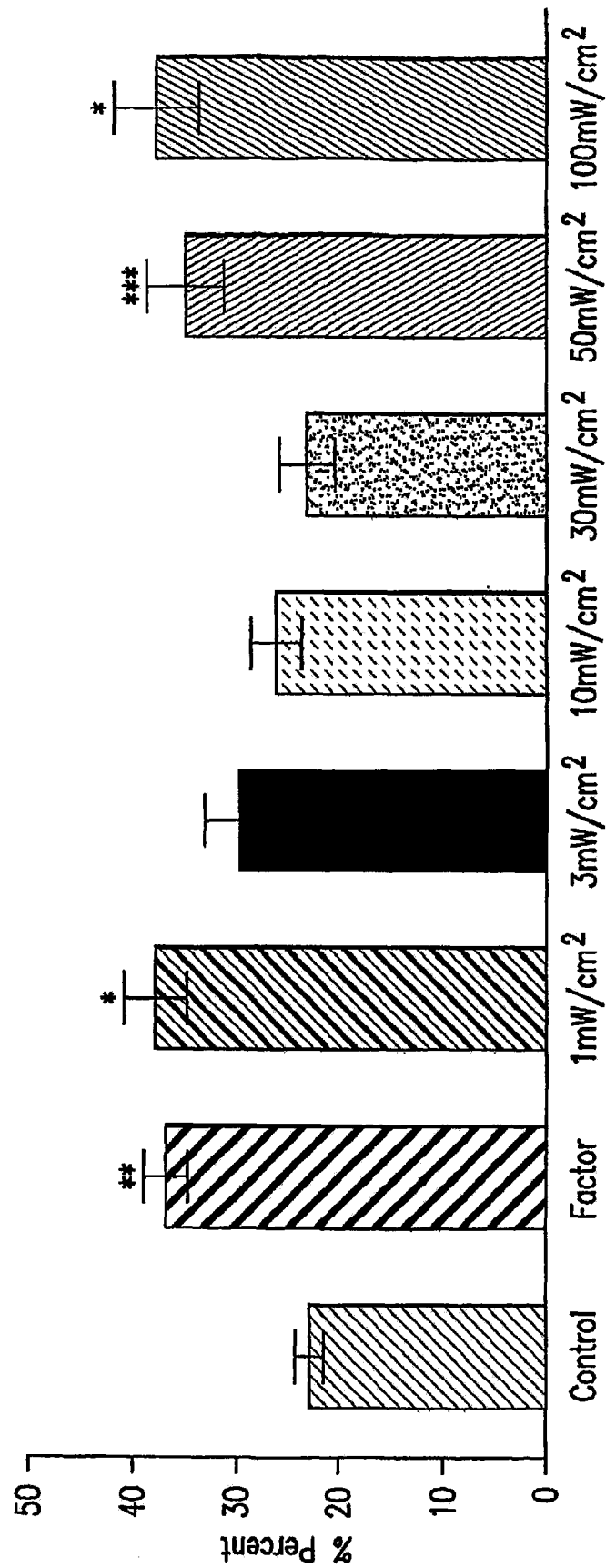
FIG. 4 shows the effect of light stimulation of different power densities on NHNPC surface area growth. NHNPCs were exposed to 810 nm light at power densities ranging from 1 mW to 100 mW once a day for three consecutive days.

The effects of various wavelengths, power densities and dosages on NHNPCs were assessed by surface area coverage. In FIGS. 3A-3E, ten wavelengths of light were tested to determine the amount of surface area growth supported. Although statistical analysis using one-way ANOVA with a Tukey post-hoc test compared all groups, significant differences are indicated for the Factors and 810 nm groups compared to the Control group. Cells subjected to Factors or 810 nm light covered significantly more surface area than the Control group (*p<0.001). Cells subjected to 515 nm light covered significantly less surface area as compared to the Factors group (p<0.001) and the Control group (p<0.0002). NHNPCs treated with 810 nm light was determined to be the optimal wavelength. In FIG. 4, cells were treated with 810 nm light at power densities of 1, 3, 10, 30, 50, and 100 mW/cm$^2$. Result shows that 1 (*p<0.01), 50 (*p<0.007), 100 mW/cm$^2$ (p<0.01) and cells treated with Factors (p<0.001) covered significantly more surface area than the Control group. Accordingly, the optimal power density for the NHNPCs was determined at 1, 50 and 100 mW/cm$^2$, since light treatment at these power densities led to cell growth comparable to the growth of the Factors treated cells. As shown in FIGS. 5A-5G, There was no statistical significance between the Factor (B,G) and 0.2 J/cm$^2$ groups (E, G). Both the Factor and 0.2 J/cm$^2$ treated NHNPCs had significantly more surface area covered compared to Control (A, G) group (*p<0.001). Based on these experiments, it was determined that the PCs respond best to 810 nm light at a dose of 0.2 J/cm$^2$, and at power densities of 1, 50 or 100 mw/cm$^2$.

Example 3

Light Treatment Promotes Neuronal Growth

Figure 6A:
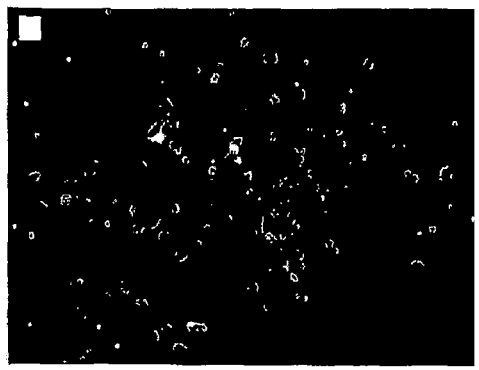
FIG. 6 is NHNPCs plated and grown under either normal conditions (A-C) (in the presence of growth factors: FGF-2 and EGF), or were treated with 810 nm light and in the absence of factors (D) for 7 days. They were fixed and processed for single label immunocytochemistry using musashi (A) and nestin (13), or double-label immunocytochemistry using TUJ1 and GFAP and counterstained with DAPI (blue) to visualize nuclei. Factor treated NHNPCs (C) and 810 nm light treated NHNPCs (D) labeled with TUJ1 (red) and GFAP (green). Bar=100 μm (A, B); 200 μm (C, D).
Figure 6B:

To characterize the NHNPCs, the expression of nestin (green, FIG. 6A), musashi (green, FIG. 6B), TUJ1 (red,) and GFAP (green) (FIG. 6C, D) were examined. Cells were grown according to the manufacturer in the presence of growth factors and were subsequently immunolabeled for the progenitor markers nestin and musashi. The NHNPCs labeled with both progenitor markers (FIGS. 6A and B), demonstrating the presence of stem/progenitor cells within the neurosphere.

Figure 6C:
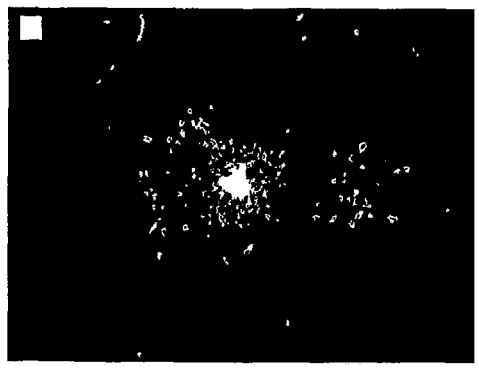
Figure 6D:
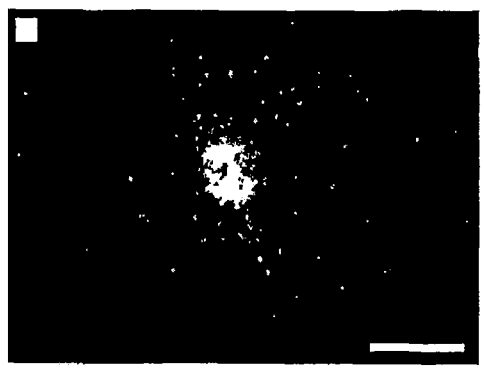

To determine if light would drive NHNPCs into specific cellular phenotypes that differed from those of NHNPCs grown in the presence of mitogens, immunocytochemistry for neuronal and glial markers was performed. NHNPCs, grown in the presence of growth factors, labeled for both the neuronal and glial markers (FIG. 6C). NHNPCs, exposed to 810 nm light (50 mW/cm$^2$, 0.2 J/cm$^2$) in the absence of growth factors, were also immunolabeled for TUJ1 and GFAP. Under normal conditions, NHNPC cultures typically co-express GFAP and TUJ1 in equivalent amounts. There was an equivalent amount of the neuronal and glial label found in both the Factors and the 50 mW/cm$^2$ group (FIGS. 6C and D), indicating that the light does not change the phenotypical morphology of the NHNPCs under these parameters.

Figure 7A:
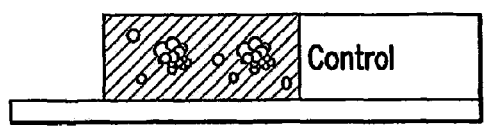
FIGS. 7A-7D are schematics showing an experimental design for treating cells with lights of different power densities.
Figure 7B:
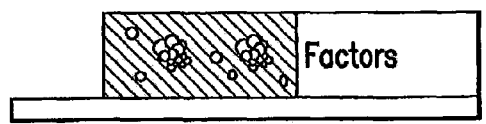
Figure 7C:
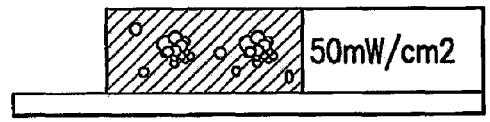
Figure 7D:
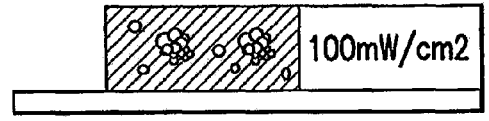

FIGS. 7A-7D are schematics showing an experimental design for treating cells with lights of different power densities. FIG. 7A is the control group, grown in standard media (neural progenitor basal medium (NPBM) plus gentamycin sulfate). The Control group received no growth factors, serum or light treatment. NHNPCs in the Factor group (B) were grown in standard media plus human recombinant (hr) EGF (20 ng/ml), hrFGF-2 (20 ng/ml), and a proprietary serum provided by the company, Cambrex (Walkersville, Md.) called neural survival factor-1 (NSF-1). Cells in the Light groups, of 50 mW/cm² (C) and 100 mW/cm² (D) were grown in standard media and treated with 810 nm light at a dose of 0.2 J/cm² for three consecutive days.

Example 4

Light Treatments' Effect on Proliferation, Neurite Outgrowth, and Migration

Figure 8A:
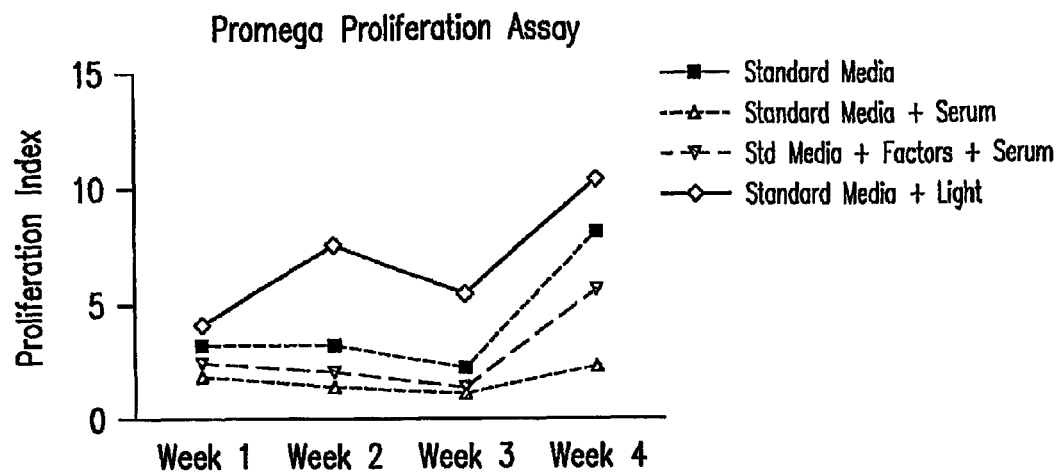
FIGS. 8 A-B are graphs of cell proliferation of NHNPCs based on metabolism (A) or DNA content (B).
Figure 8B:
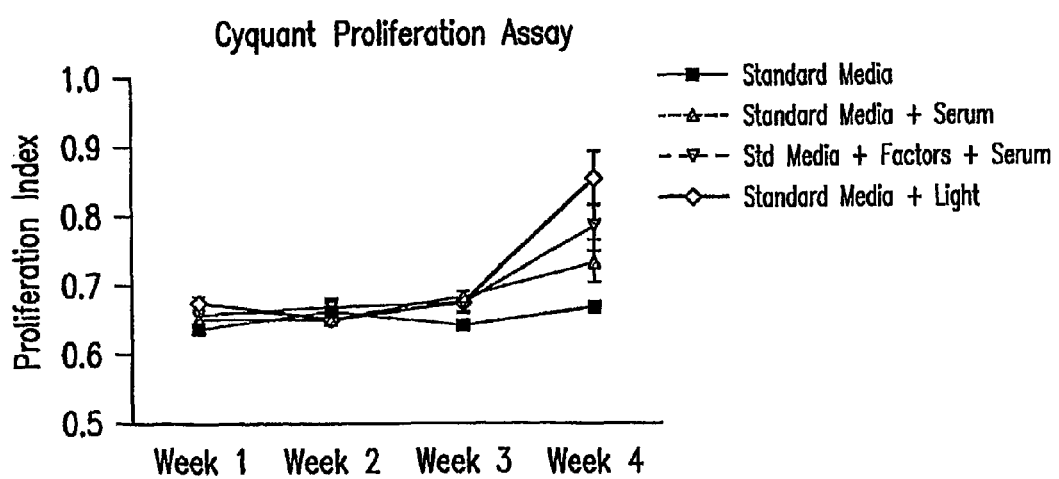

The Promega proliferation assay was performed to measure the metabolic activity of viable cells based on the bioreduction of the tetrazolium salt MTS into formazan, which is directly proportional to the number of living cells. As shown in FIG. 8A, cells from each group were plated. The Standard media+Light group was treated for three consecutive days, grown for an additional four days, and treated once a week until the conclusion of the experiment. Measurements were analyzed in triplicate at 1, 2, 3 and 4 weeks. Statistical analysis was performed using a one-way ANOVA with a Tukey post hoc test. At weeks 1, 2, 3 and 4, the Standard media+Light group had significantly increased proliferation/metabolic activity as compared to the Standard media+factors+serum, Standard media and Standard media+serum groups ($p<0.001$). The Standard media+factors+serum group had significantly greater proliferation than the Standard media+serum group ($p<0.001$) at all four time points. Data are presented as the mean±SEM. The Standard media+factors+serum and Standard media+serum groups were decreased over the 4 weeks as compared to the remaining two groups The Cyquant proliferation assay was performed to determine cell proliferation based on DNA content of the sample. As shown in FIG. 8B, measurements were analyzed in triplicate at 1, 2, 3 and 4 weeks. Statistical analysis was performed using a one-way ANOVA with a Tukey post hoc test. At weeks 1, 2, and 3, there was no statistical difference in proliferation between any of the four groups. By week 4, the Standard media+Light group had significantly increased proliferation as compared to the Standard media group ($p<0.01$). Data are presented as the mean±SEM. The manufacturer of the cells confirms that these cells have a very low to negligible proliferation rate.

To determine if light influenced neurite outgrowth of the NHNPCs, immunocytochemistry for the neuronal migration marker, doublecortin, was performed (FIGS. 9A-E). Neurite outgrowth was assessed and plotted for each group (FIG. 9F). The negative control slide (FIG. 9A) did not contain any DCX labeling. NHNPCs were placed into three groups: Control, Factors, and Light treated. The Factors (D, F) and Light treated (E, F) groups had significantly longer neurite outgrowth (*$p<0.001$) as compared to the Control group (C, F). The Factors and Light treated groups were not significantly different from one another. Bar=200 μm. These results support the hypothesis that light is capable of inducing neurite outgrowth of NHNPCs in the absence of mitogenic factors.

To determine the effect of light on NHNPC migration, naïve NHNPCs were exposed to either 1) starvation media; 2) factor media (contained growth factors and serum); 3) light conditioned starvation media taken from 810 nm, 50 mW/cm², 0.2 J/cm² for three consecutive days treated cultures; or 4) light treated starvation media (starvation media treated with 810 nm light, 50 mW/cm², 0.2 J/cm²; for three consecutive days in the absence of cells) for an additional 24 hrs and analyzed.

Figure 10:
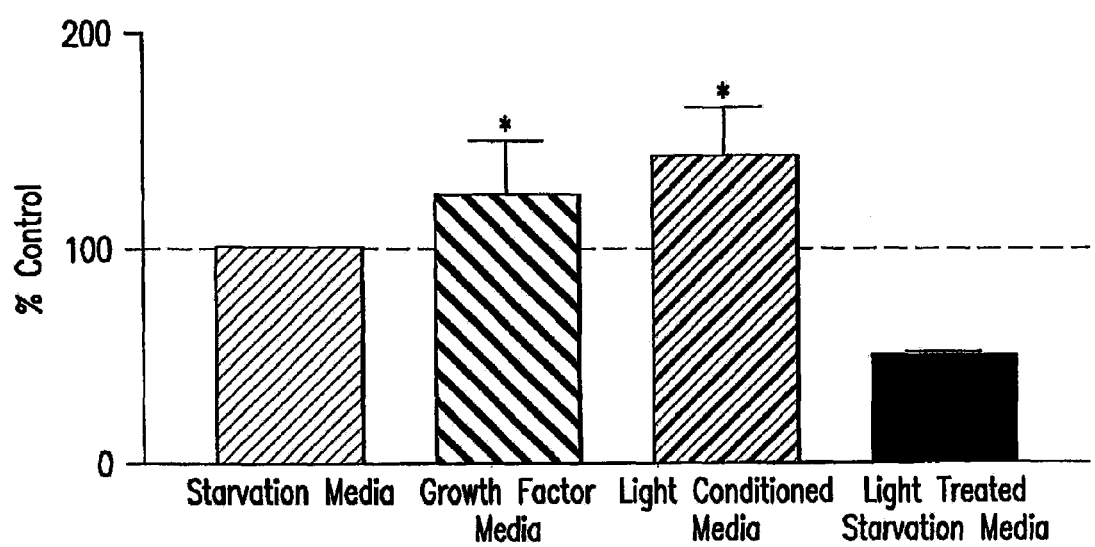
FIG. 10 is a graph showing the migration of naïve NHNPCs, defined as NHNPCs that were not exposed to growth factors, serum or light treatment. These cells were starved for 18-24 hrs prior to the assay. They were then placed into one of four types of attractant medium for 24 hours: 1) Starvation media: contains no growth factors; 2) Growth Factor media: contains EGF and FGF-2; 3) Light Conditioned Cell Media: media taken from cells exposed to 810 nm, 50 $mW/cm^2$ light for three consecutive days; or 4) Light Treated Starvation Media: starvation media treated with 810 nm, 50 $mW/cm^2$ light for three consecutive days. Data represented as the mean±SEM of optical densities minus the optical density of the blank control divided by the mean of the Starvation Media data, expressed as % Control.

As shown in FIG. 10, naïve NHNPCs exposed to the factor media (**$p<0.05$) and light conditioned starvation media (*$p<0.01$) had a significant increase in migration as compared to the starvation and light treated starvation medias (one-way ANOVA $p=0.002$). Migration between the factor media and light conditioned starvation media groups was comparable. These data suggest that an undetermined factor(s) was secreted into the media by cells that were treated with the 810 nm light, and was capable of supporting migration.

Example 5

Light Treatment Induces Mitogen Production in NHNP Cells

The production of FGF-2 was investigated to determine whether there was an up-regulation or a de-regulation of the mitogenic factor following treatment, using immunocytochemistry at the completion of the study.

Figure 11:
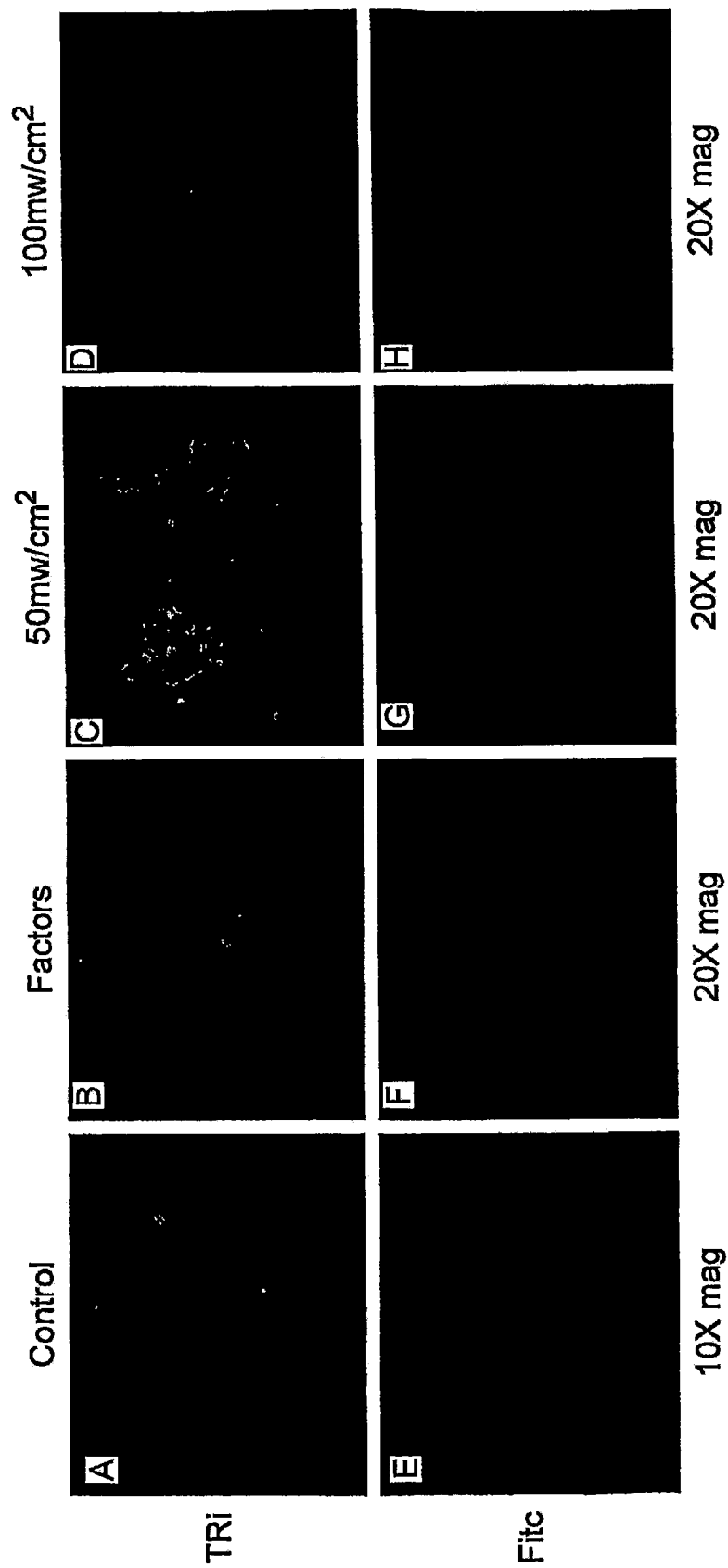
FIG. 11 is a composite of images showing the immunocytocharacterization of the mitogen FGF-2 in NHNPCs. NHNPCs were separated into four groups: Control, Factors, 50 $mw/cm^2$ and 100 $mw/cm^2$. The Light Treated slides were treated with 810 nm light for three consecutive days. All groups of cells were grown for a total of 7 days, at which time they were fixed and processed for FGF-2 (green) immunocytochemistry and counterstained with DAPI (blue) to visualize nuclei. The Control group had minimal endogenous FGF-2 label. Bar=100 μm (Control); 200 μm (Factors, 50 and 100 $mw/cm^2$).

Initial immunocytochemistry was performed to identify endogenous FGF-2 within the groups. To evaluate a possible mechanism of the effect of light on growth and differentiation, initial immunocytochemistry was performed to determine the endogenous production of the mitogen FGF-2. As shown in FIG. 11, the Factors group, grown in the presence of the mitogens FGF-2 and EGF, showed an increased amount of FGF-2 label. The Light Treated groups, grown in the absence of mitogens, but treated with 810 nm light, had increased endogenous FGF-2 expression compared to the Control group, but less than the Factors group. The 50 mW/cm² had comparable levels to the Factor group, which were observed to be greater than the Control and 100 mW/cm² groups. The presence of FGF-2 in the Light treated groups indicate that light is acting to induce the production of endogenous FGF-2 within these cells, which facilitates survival and proliferation.

Initial RT-PCR was performed to determine if the groups expressed mRNA for certain growth factors including FGF-2, EGF, BDNF and NGF. As shown in FIG. 12, NHNPCs were placed into four groups: Control, Factors, Light treated (3 days) and Light treated (7 days). Cells in the Control group were grown in standard media (NPBM plus gentamycin sulfate). Factor group cells were grown in standard media plus human recombinant (hr) EGF (20 ng/ml), hrFGF-2 (20 ng/ml), and NSF-1. Cells in the Light groups were grown in standard media and treated with light (810 nm, 0.2 J/cm², 50 mW/cm²) for three consecutive days. All cells were plated on laminin coated-chamber slides at a seeding density of 25,000 cells/cm². Control, Factors, and Light treated (7 days) cells were harvested 7 days in vitro while the Light treated (3 days) cells were harvested at 3 days in vitro, after which RT-PCR was performed. Primers were designed for FGF-2, EGF, BDNF, NGF, and β-actin.

Figure 12A:
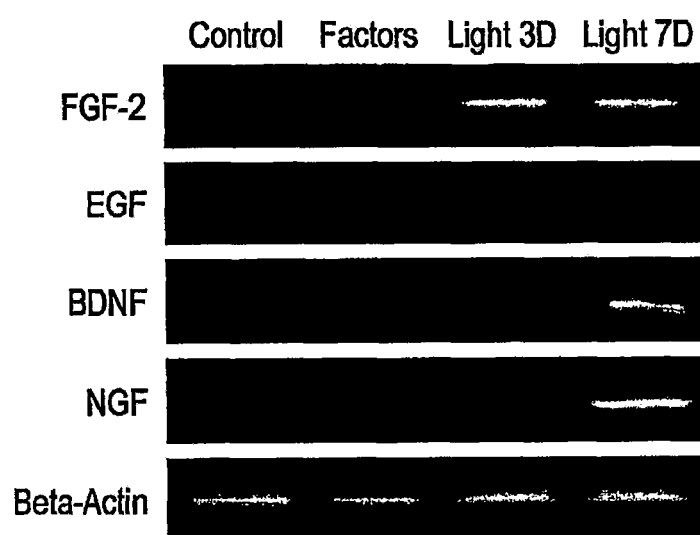
FIGS. 12A-E are a composite of mRNA expression of FGF-2, EGF, BDNF, NGF and β-actin. NHNPCs were placed into four groups: Control, Factors, 50 mw/cm2 (3 days), and 50 $mw/cm^2$ (7 days). The Light Treated slides were treated (810 nm light, 50 $mw/cm^2$, 0.2 $J/cm^2$) for three consecutive days. All groups, with the exception of the 50 $mw/cm^2$ (3 days) were grown for a total of 7 days. Total cellular RNA was extracted and RT-PCR was performed. (A) NHNPCs mRNA expression levels in the four groups for FGF-2, EGF, BDNF, and NGF. (B) The 3D and 7D Light groups had significantly greater FGF-2 expression than the Control ($p<0.01$) and Factors groups ($p<0.01$; $p<0.05$ respectively). (C) All groups expressed EGF mRNA. (D)) The two Light groups and the Factors group had significantly greater BDNF expression than the Control group ($p<0.05$). (E) The 7D Light group had significantly greater NGF expression than the remaining three groups ($p<0.001$), while the 3D Light group had significantly greater NGF expression than the Control and Factors groups ($p<0.001$).
Figure 12B:
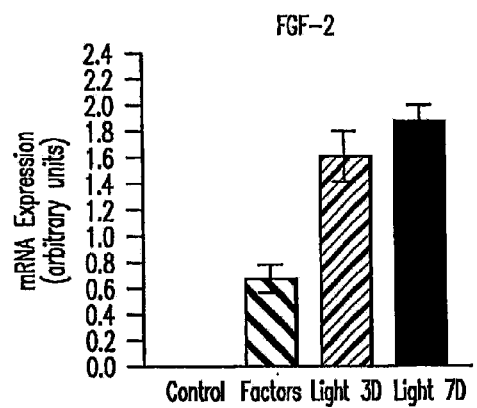
Figure 12C:
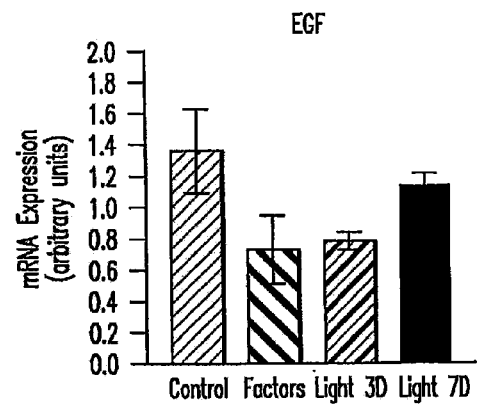
Figure 12D:
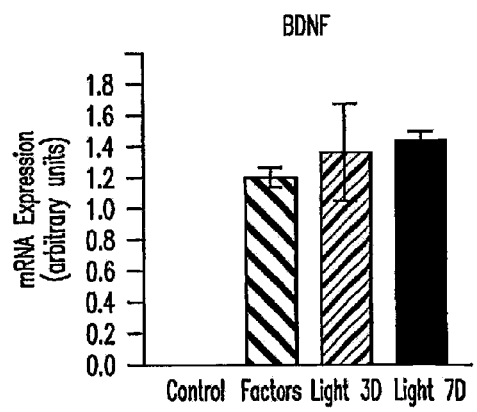
Figure 12E:
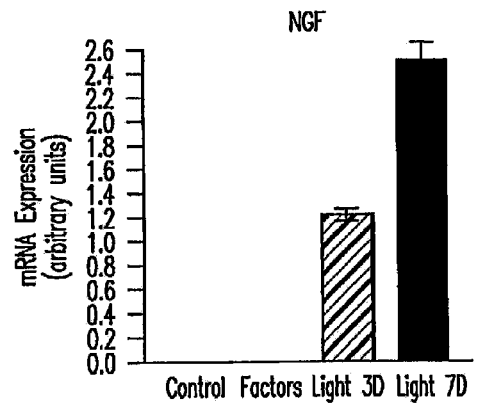

FIG. 12A is PCR gene expression for FGF-2, EGF, BDNF, NGF and β-actin. FIGS. 12B-E are the semi-quantitative measurement for FGF-2, EGF, BDNF and NGF. The measurement of arbitrary intensity units of each band was determined using Multi Gauge (www.lifescience.fujifilm.com), and values were normalized based on the β-actin sample. This experiment was repeated twice. The graphs are averages of both ratios for each growth factor. Results show that all groups expressed EGF mRNA (FIG. 12C). The two Light groups and the Factors group had significantly greater BDNF expression than the Control group ($p<0.05$) FIG. 12D). As shown in FIG. 12E, the 7D Light group had significantly greater NGF expression than the remaining three groups ($p<0.001$), while the 3D Light group had significantly greater NGF expression than the Control and Factors groups ($p<0.001$).

Table 1 represents a summary of the levels of growth factor expression based on the semi-quantitative method.

TABLE 1

| Growth Factor | Control | Factor | Light 3D | Light 7D |
|---|---|---|---|---|
| FGF2 | − | + | ++ | ++ |
| FGF | ++ | + | + | + |
| BDNF | − | + | + | + |
| NGF | − | − | + | ++ |

Figure 13:
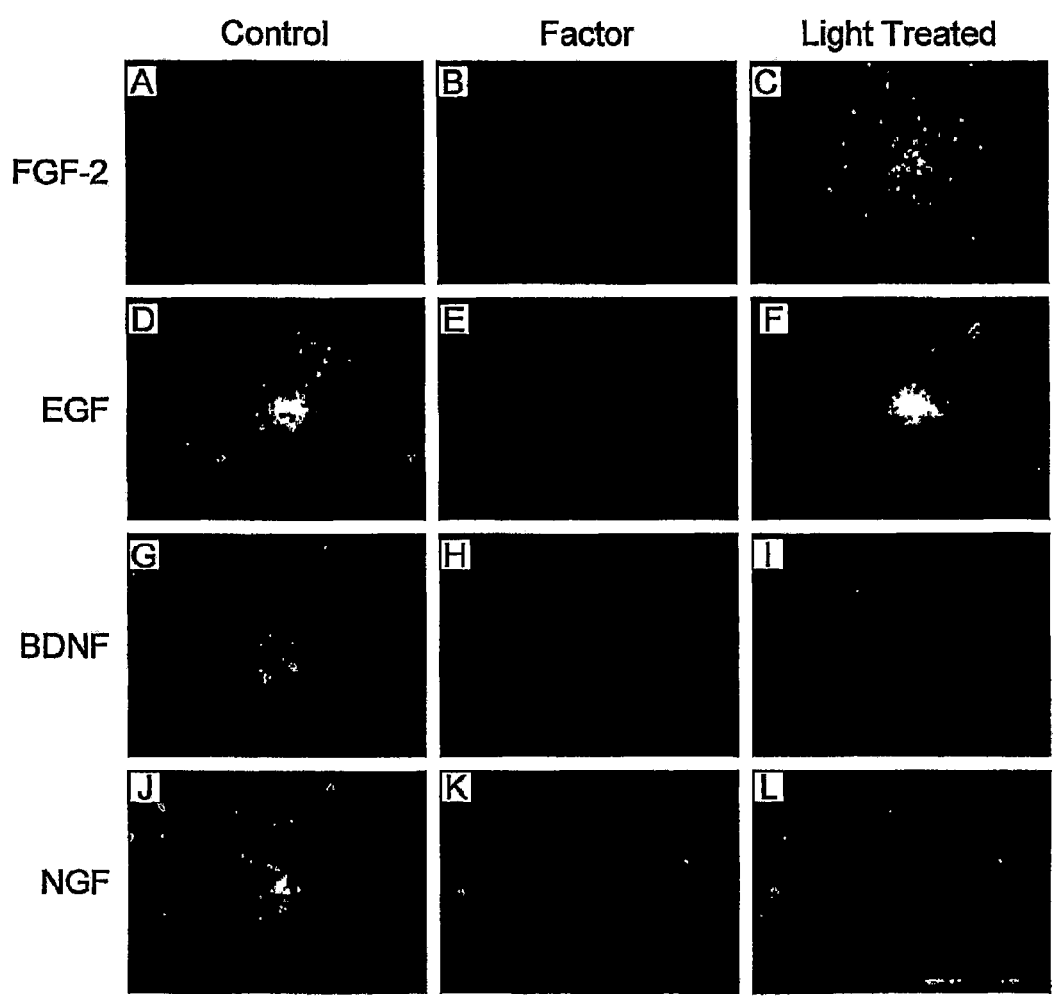
FIGS. 13A-L is a composite of protein expression of growth factors in NHNPCs in three groups. NHNPCs were separated into three groups: Control, Factors, and Light Treated. The Light Treated slides were treated 810 nm light, 50 $mw/cm^2$, 0.2 $J/cm^2$ for three consecutive days. All groups of cells were grown for a total of 7 days, at which time they were fixed and processed for FGF-2, EGF, BDNF, and NGF (red) immunocytochemistry and counterstained with DAPI (blue) to visualize nuclei.
Figure 14:
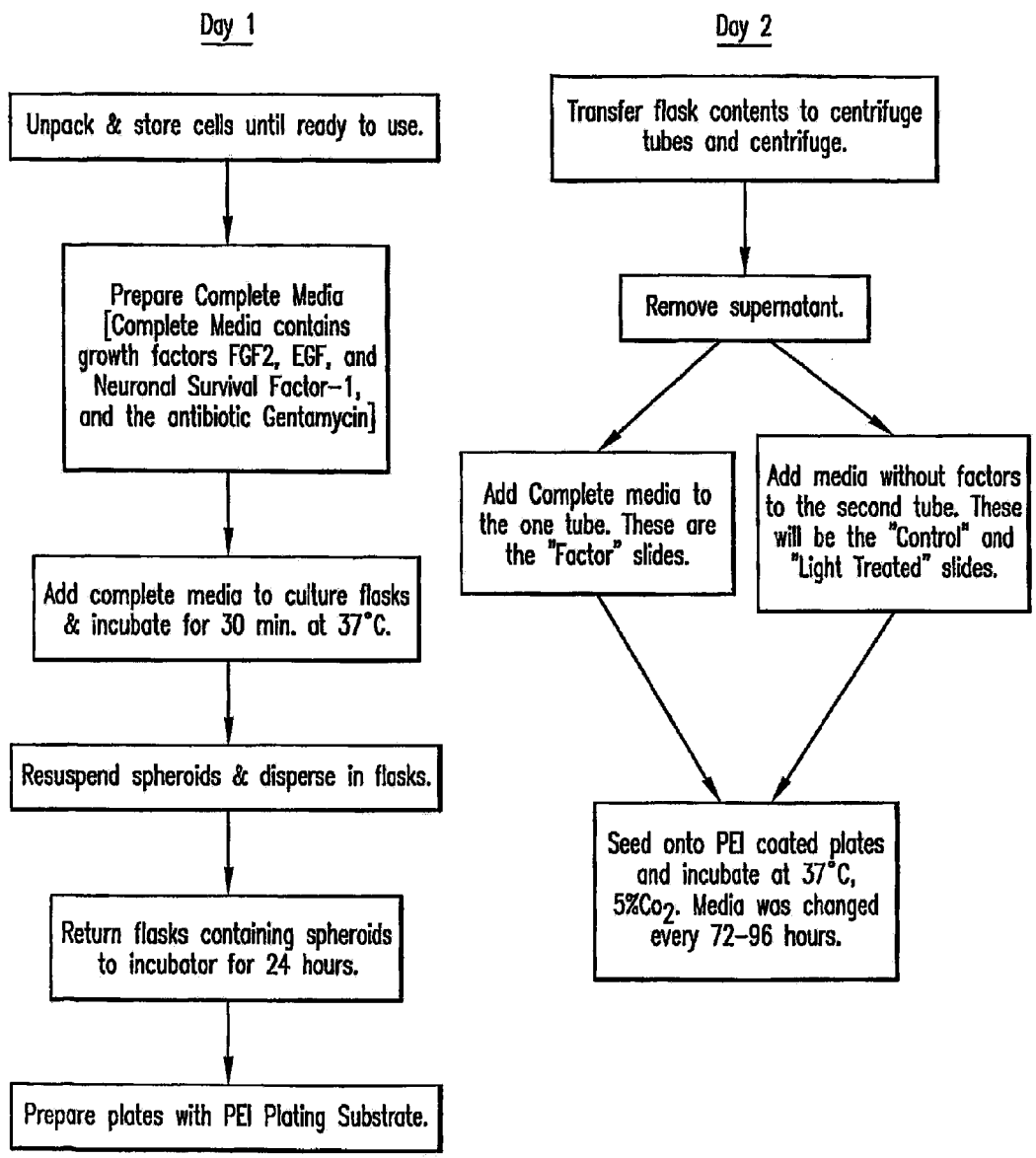
FIG. 14 is the overview of NHNP culture process.

Protein expression of FGF-2, EGF, BDNF, and NGF in NHNPCs is shown in FIG. 13. NHNPCs were placed into three groups: Control, Factors and Light treated. The Light treated slides were treated with 810 nm light for three days. The NHNPCs from the groups were fixed and processed for immunocytochemistry at 7 days in vitro (Scale Bar=200 μm).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for providing differentiated cells in a subject in need thereof comprising:
   exposing neural progenitor cells ex vivo to a laser light source having a wavelength within the range of 200-1500 nm at a power density of 0.001-500 mW/cm$^2$ to yield light stimulated cells, wherein said light stimulated cells undergo neuronal differentiation ex vivo; and
   transplanting said light stimulated cells into the subject in need thereof.

2. The method of claim 1, further comprising, prior to said transplanting step, culturing said light stimulated cells in vitro under a condition that promotes differentiation of said cells.

3. The method of claim 1, wherein said laser light source has a wavelength within the range of 400-1200 nm and is applied at a power density of 0.5-150 mW/cm$^2$.

4. The method of claim 3, wherein said laser light source has a wavelength within the range of about 750-1000 nm and is applied at a power density of 0.1-200 mW/cm$^2$.

5. The method of claim 4, wherein said laser light source has a wavelength of about 810 nm and is applied at a power density of about 1 mW/cm$^2$, about 50 mW/cm$^2$ or about 100 mW/cm2.

6. The method of claim 1, wherein said subject has a central nervous system (CNS) injury or a peripheral nervous system (PNS) injury.

7. The method of claim 6, wherein said CNS injury or PNS injury is spinal cord injury, stroke or traumatic brain injury.

8. The method of claim 1, wherein said subject has a neurodegenerative disease.

9. The method of claim 8, wherein said neurodegenerative disease is selected from the group consisting of Parkinson's disease, Alzheimer's disease, Huntington's disease, Multiple Sclerosis, and ALS.

10. The method of claim 1, wherein the subject is a mammal.

11. A method for treating CNS injury or PNS injury in a subject in need thereof, said method comprising:
    exposing human neural progenitor cells ex vivo to a laser light source having a wavelength within the range of 200-1500 nm at a power density of 0.001-500 mW/cm$^2$ to yield light stimulated cells, wherein said light stimulated cells undergo neuronal differentiation ex vivo; and
    transplanting the light stimulated cells into the subject.

12. The method of claim 11, further comprising, prior to said transplanting step, culturing said human neural progenitor cells in vitro under a condition that promotes differentiation or proliferation of said cells.

13. The method of claim 11, wherein said laser light source has a wavelength of about 810 nm and is applied at a power density of about 1 mW/cm$^2$, about 50 mW/cm$^2$ or about 100 mW/cm$^2$.

14. The method of claim 11, wherein said CNS injury or PNS injury is spinal cord injury, stroke or traumatic brain injury.

* * * * *

UNITED STATES PATENT AND TRADEMARK OFFICE
CERTIFICATE OF CORRECTION

Page 1 of 1

PATENT NO. : 9,205,276 B2
APPLICATION NO. : 11/909145
DATED : December 8, 2015
INVENTOR(S) : Tara B. Romanczyk et al.

It is certified that error appears in the above-identified patent and that said Letters Patent is hereby corrected as shown below:

On the title page,
    Item (75) Inventors: please replace "Ronald R. Wayant" with -- Ronald W. Wayant --.

Signed and Sealed this
Tenth Day of May, 2016

Michelle K. Lee
*Director of the United States Patent and Trademark Office*